United States Patent [19]

Marler et al.

[11] Patent Number: 5,072,054
[45] Date of Patent: Dec. 10, 1991

[54] PROCESS FOR PREPARING SHORT CHAIN ALKYL PHENOLS

[75] Inventors: David O. Marler, Deptford; John P. McWilliams, Woodbury; Charles M. Smith, Princeton, all of N.J.

[73] Assignee: Mobil Oil Corp., Fairfax, Va.

[21] Appl. No.: 560,401

[22] Filed: Jul. 31, 1990

Related U.S. Application Data

[63] Continuation-in-part of Ser. No. 470,015, Jan. 25, 1990, Pat. No. 4,954,663, which is a continuation-in-part of Ser. No. 254,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .................. C07C 37/14; C07C 37/16; C07C 37/18
[52] U.S. Cl. .................. 568/794; 568/790; 568/791
[58] Field of Search .................. 568/790, 791, 794

[56] References Cited

U.S. PATENT DOCUMENTS

| | | | |
|---|---|---|---|
| 4,283,573 | 8/1981 | Young | 568/794 |
| 4,391,998 | 7/1983 | Wu | 568/781 |
| 4,439,409 | 3/1984 | Puppe et al. | 423/328 |
| 4,665,238 | 5/1987 | Imai et al. | 568/794 |
| 4,826,667 | 5/1989 | Zones et al. | 423/277 |
| 4,954,663 | 9/1990 | Marler et al. | 568/791 |

FOREIGN PATENT DOCUMENTS 0231860  8/1987  European Pat. Off. .
0293032  11/1988 European Pat. Off. .

*Primary Examiner*—Werren B. Lone
*Attorney, Agent, or Firm*—Alexander J. McKillop; Charles J. Speciale; Dennis P. Santini

[57] ABSTRACT

Short-chain alkyl phenols are prepared by reacting an alkylatable phenolic compound with an alkylating agent having one or more available alkylating aliphatic groups of from one to five carbon atoms. The reaction is carried out under alkylation conditions with a zeolite catalyst characterized by x-ray diffraction values as set forth in Tables A to D, infra.

18 Claims, No Drawings

PROCESS FOR PREPARING SHORT CHAIN ALKYL PHENOLS

CROSS-REFERENCE TO RELATED APPLICATIONS

This application is a continuation-in-part of U.S. patent application Ser. No. 07/470,015 filed Jan. 15, 1990, U.S. Pat. No. 4,954,663 which is a continuation-in-part of U.S. patent application Ser. No. 254,524 filed Oct. 6, 1988, U.S. Pat. No. 4,954,325 which is a continuation-in-part of U.S. patent application Ser. No. 98,176 filed Sept. 18, 1987 ABN, which is a continuation-in-part of U.S. patent application Ser. No. 890,268 filed July 29,1986 ABN.

BACKGROUND OF THE INVENTION

This invention relates to a process for preparing short chain alkyl phenols by alkylating an aromatic compound with a relatively short chain alkylating agent employing a synthetic porous crystalline material, or zeolite, as alkylation catalyst.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1.2. The electrovalence of the tetrahedra containing the Group IIIA element, e.g., aluminum, is balanced by the inclusion in the crystal of a cation, e.g., an alkali metal the ratio of the Group IIIA element, e.g., aluminum, to the number of various cations, such as Ca, Sr, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), zeolite ZSM-35 (U.S. Pat. No. 4,016,245), and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Patent Nos. 4,061,724, 4,073,85 and 4,104,294 describe crystalline silicates of varying alumina and metal content.

Short chain alkylphenols are commercially important end products and process intermediates. As end products they are used as antioxidants, stabilizers, and additives, for example, as radical trapping agents in plastics, elastomers, synthetic fibers, fuels, lubricants, and foods. As intermediates they are used, for example, in oxidation reactions to produce hydroquinones.

Production of these compounds by conventional methods, for example, by the alkylation of phenol in the presence of conventional alkylation catalysts, is, however, somewhat problematic in that the reaction yields a broad spectrum of products. Isolation or enrichment of specific positional isomers is both difficult and expensive.

Traditionally, alkylation reactions are generally carried out at atmospheric pressure with the reactants in the liquid phase utilizing catalysts such as sulfuric acid, boron trifluoride, aluminum chloride or strongly acidic ion exchange resins. Some zeolites, specifically REX and HY, have been reported in the scientific literature as catalyzing the reaction of a relatively long chain alkylating agent, i.e. 1-decyl alcohol, with phenol at atmospheric pressure and 200° C. the product of that reaction was predominantly an ortho/para mixture of decylphenols with side chain attachment largely at the second and third carbon atoms of the alkyl group.

U.S. Pat. No. 4,283,573 describes a process for producing relatively long chain alkylphenols by alkylation of phenol with a long chain alkylating agent possessing one or more available alkyl groups of at least 5 carbon atoms in length employing as catalyst a zeolite such as cancrinite, gmelinite, mordenite, offretite or ZSM-12.

While zeolites, such as ZSM-12, have found utility in producing relatively long chain alkylphenols, it is desirable to have higher selectivity and conversion ratios for the production of short chain alkyl phenols than ZSM-12 can provide.

SUMMARY OF THE INVENTION

In accordance with the present invention, a process for the production of relatively short chain alkyl-substituted phenolic compounds is provided which comprises contacting at least one alkylatable phenolic compound with at least one alkylating agent possessing an alkylating aliphatic group having from one to five carbon atoms under alkylation reaction conditions and in the presence of an alkylation catalyst to provide an alkylated phenolic compound possessing at least one alkyl group derived from said alkylating agent. The catalyst comprises a synthetic porous crystalline material characterized by an X-ray diffraction pattern substantially as set forth in Tables A to D, infra.

DESCRIPTION OF THE SPECIFIC EMBODIMENTS

The invention contemplates the reaction of alkylatable phenolic compounds with alkylating agents possessing a relatively short chain alkylating group, i.e., of from one to five carbon atoms. The preferred alkylatable compound is phenol, but other phenolic reactants can be u to yield a variety of alkylation products. Nonlimiting examples of phenolic compounds which can be used as feed herein include methylphenols (cresols); dimethylphenols (xylenols); ethyl, propyl and butyl phenols; halophenols (e.g., chloro and bromo); alkylhalophenols; alkoxyphenols; dihydroxybenzenes (e.g., hydroquinone, catechol, resorcinol); hydroxylated fused ring systems, e.g., naphthols, anthranols and phenanthranols, and so forth.

The alkylating agents which are useful in the process of this invention generally include any aliphatic or aromatic organic compound having one or more available alkylating aliphatic groups capable of reaction with the alkylatable phenolic compound. The alkylatable group itself should have from one to five carbon atoms.

Examples of suitable alkylating agents are olefins such as ethylene, propylene, butenes and pentenes, alcohols (inclusive of monoalcohols, dialcohols, trialcohols, etc.) such as methanol, ethanol, normal and isopropanols, butanols, and pentanols;, and alkyl halides such as methyl chlorides, ethyl chlorides, propyl chlorides; and higher homologs of the foregoing. The alkylating agents can be straight or branched chain compounds.

The alkylation process of this invention is conducted such that the organic reactants, i.e., the alkylatable phenolic compound and the alkylating agent, are brought into contact with the zeolite catalyst in a suitable reaction zone, such as for example a fixed bed of the catalyst, under effective alkylation conditions. Such conditions include a temperature of between about 50° C. and about 500° C., a pressure of from about 0.1 to about 100 atmospheres, a feed weight hourly space velocity (WHSV) of between about 0.1 and about 200 hr$^{-1}$ and an alkylatable phenolic compound to alkylating agent mole ratio of from about 0.1:1 to about 50:1. The WHSV is based upon the weight of the catalyst compositions employed, i.e., the total weight of active catalyst (and binder if present). Preferred reaction conditions include a temperature within the approximate range of from about 100° C. to about 400° C., a pressure of from about atmospheric to about 25 atmospheres, a feed WHSV of from about 1 to about 50 and an alkylatable phenolic compound to alkylating agent mole ratio of from about 0.5:1 to about 5:1. The reactants can be in either the vapor phase or the liquid phase and can be neat, i.e., free from intentional admixture or dilution with other material, or they ca be brought into contact with the zeolite with the air of carrier gases or diluents such as, for example, hydrogen or nitrogen.

The alkylation process described herein may be carried out as a batch-type, semi-continuous or continuous operation utilizing a fixed or moving bed catalyst system. A further embodiment entails use of a catalyst zone wherein the hydrocarbon charge is passed concurrently or countercurrently through a moving bed of particleform catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

The product(s) of the alkylation reaction may be used as end products, or as intermediates. One embodiment of the present invention employs the catalyst of the present invention in the preparation of o-, m-, and p-dihydroxybenzenes (i.e., catechol, resorcinol, and hydroquinone, respectively) from phenol. For example, phenol can be alkylated with propylene to produce a mixture of isopropyl phenol isomers. The mixture can be charged to an oxidation reactor, or may optionally be separated such that only one of the isomers is charged to the oxidation reactor, the others being recycled to the alkylation reaction.

Oxidation of isopropyl phenol can be performed by known technology described, for example, in U.S. Patent Nos. 3,883,600 and 4,053,520, both of which are hereby incorporated by reference in their entirety. Oxidation of the isopropyl phenol produced a hydroperoxide, which can then be subjected to acid cleavage in accordance with known methods to produce the dihydroxybenzene and acetone. A method for the cleavage of isopropylbenzene hydroperoxide which can be employed in the present method is described in U.S. Pat. No. 3,923,908, hereby incorporated by reference in its entirety.

Thus, the present invention offers a convenient way to produce hydroquinone, catechol, etc. from phenol. Prior known methods which alkylated benzene to produce diisopropylbenzene via cumene, e.g., U.S. Pat. No. 3,927,134 herein incorporated by reference, are characterized by steric hinderance which prevents the formation of catechol. Moreover, the instability of the dihydroperoxide intermediate results in selectivities lower than those observed in the corresponding phenol process of the present invention.

The catalyst particles employed in the process of the present invention are typically provided as composites of the synthetic porous crystalline material and a binder, e.g., In its calcined form, the synthetic porous crystalline material useful for the catalytic process described herein is characterized by an X-ray diffraction pattern including the following lines:

TABLE A

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | M-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |

TABLE B-continued

| Interplanar d-Spacing (A) | Relative Intensity, $I/I_o \times 100$ |
|---|---|
| 6.00 ± 0.10 | W-M |
| 4.06 ± 0.07 | W-S |
| 3.91 ± 0.07 | M-VS |
| 3.42 ± 0.06 | VS |

More specifically, the calcined form of the synthetic porous crystalline material may be characterized by an x-ray diffraction pattern including the following lines:

TABLE C

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

More specifically, the synthetic porous crystalline material may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_0$, where $I_0$ is the intensity of the strongest line or peak, and d (obs.) the interplanar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

W=0-20
M=20-40
S=40-60
VS=60-100

It should be understood that these X-ray diffraction patterns are characteristic of all species of this synthetic porous crystalline material. The sodium form as well as other cationic forms reveal substantially the same pattern with some minor shifts in interplanar spacing and variation in relative intensity. Other minor variations can occur depending on the ratio of structural components, e.g., silicon to aluminum mole ratio of the particular sample, as well as its degree of thermal treatment.

Examples of such porous crystalline materials include the PSH-3 composition of U.S. Pat. No. 4,439,409, incorporated herein by reference, and the crystalline material of U.S. Application Ser. No. 254,524, incorporated herein by reference, and referred to herein as "MCM-22".

MCM-22 has a composition involving the molar relationship:

$X_2O_3:(n)YO_2$, wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, MCM-22 has a formula, on an anhydrous basis and in terms of moles of oxides per n moles of $YO_2$, as follows:

$(0.005-0.1)Na_2O:(1-4)R:X_2O_3:nYO_2$ wherein R is an organic component. The Na and R components are associated with the synthetic porous crystalline material as a result of their presence during crystallization, and are easily removed by post-crystallization methods hereinafter more particularly described.

MCM-22 is thermally stable and exhibits a high surface area greater than about 400m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Preferred cations are those which tailor the activity of the catalyst. These include hydrogen, rare earth metals and metals of Groups IIA, IIIA, IVA, IB, IIB, IIIB, IVB and VIII of the Periodic Table of the Elements.

In its calcined form, MCM-22 appears to be made up of a single crystal phase with little or no detectable impurity crystal phases and has an X-ray diffraction pattern including the lines listed in above Tables A-D.

Prior to its use in the catalyst composition herein, the synthetic porous crystalline material zeolite should be subjected to thermal treatment to remove part or all of any organic constituent present therein.

The synthetic porous crystalline material present in the catalyst composition herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the synthetic porous crystalline material and/or matrix with which the synthetic porous crystalline material may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the synthetic porous crystalline material such as, for example, by, in the case of platinum, treating the synthetic porous crystalline material with a solution containing the platinum metal-containing ion. Thus, suitable platinum compounds for this purpose include chloroplatinic acid, platinous chloride and various compounds containing the platinum amine complex.

The synthetic porous crystalline material, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal temperature can be performed at a temperature of up to about 925° C.

Prior to its use in the catalyst composition and process of this invention, the crystals of synthetic porous crystalline material should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the crystalline material in a vacuum but a longer time will be required to achieve a suitable degree of dehydration.

MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, or organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing MCM-22, the $YO_2$ reactant contains a substantial amount of solid $YO_2$, e.g., at least about 30 wt.% solid $YO_2$. Where $YO_2$ is silica, the use of a silica source containing at least about 30 wt.% solid silica, e.g., Ultrasil (a precipitated, spray dried silica containing about 90 wt.% silica) or HiSil (a precipitated hydrated $SiO_2$ containing about 87 wt.% silica, about 6 wt.% free $H_2O$ and about 4.5 wt.% bound $H_2O$ of hydration and having a particle size of about 0.02 micron) favors MCM-22 crystal formation from the above mixture and is a distinct difference over the synthesis method disclosed in U.S. Pat. No. 4,439,409. If another source of oxide of silicon, e.g., Q-Brand (a sodium silicate comprised of 7 about 28.8 wt.% of $SiO_2$, 8.9 wt.% $Na_2O$ and 62.3 wt.% $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt.% solid $YO_2$, e.g., silica, and more preferably at least about 40 wt.% solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 material will vary with the nature of the reaction mixture employed and the crystallization conditions. In all cases, synthesis of the MCM-22 crystals is facilitated by the presence of at least about 0.01 percent, preferably about 0.10 percent and still more preferably about 1 percent, seed crystals based on the total weight of the crystalline product formed.

The crystals can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desirable to incorporate the synthetic porous crystalline material with another material, i.e., a binder, which is resistant to the temperatures and other conditions employed in the process of this invention. Suitable binder materials include active and inactive materials and synthetic or naturally occurring zeolite as well as inorganic materials such as clays, silica and/or metal oxides such as alumina. The latter can be either naturally occurring or provided in the form of gelatinous precipitates or gels including mixtures of silica and metal oxides. Use of a binder material in conjunction with the zeolite, i.e., combined therewith or present during its synthesis, which itself is catalytically active may change the conversion and/or selectivity of the catalyst. Inactive materials suitable serve as diluents to control the amount of conversion so that products can be obtained economically and in a controlled fashion without having to employ other means for controlling the rate of reaction. These materials can be incorporated into naturally occurring clays, e.g., bentonite and kaolin, to improve the crush strength of the catalyst under commercial operating conditions. Good crush strength is an advantageous attribute for commercial use since it prevents or delays breaking down of the catalyst into powder-like materials. Said materials, i.e., clays, oxides, etc., function as binders for the catalyst. Clay binders have been employed normally only for the purpose of improving the crush strength of the catalyst.

Naturally occurring clays which can be composited with the zeolite crystals include the montmorillonite and kaolin family, which families include the subbentonites, and the kaolines commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

Apart from or in addition to the foregoing binder materials, the zeolite crystals can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may also be advantageous to provide at least a part of the foregoing matrix materials in colloidal form so as to facilitate extrusion of the bound catalyst component(s).

The relative proportions of finely divided crystalline material and inorganic oxide matrix can vary widely with the zeolite content ranging from about 1 to about 90 percent by weight and more usually, particularly when the composite is prepared in the form of beads, in the range of about 2 to about 80 weight percent of the composite.

The stability of MCM-22 may be increased by steaming. U.S. Patent Nos. 4,663,492; 4,594,146; 4,522,929; and, 4,429,176, the entire disclosures of which are incorporated herein by reference, describe conditions for the steam stabilization of zeolite catalysts which can be utilized to steam-stabilize the catalyst for use herein. The steam stabilization conditions include contacting the catalyst with, e.g., 5-100% steam at a temperature of at least about 300° C. (e.g., 300-650° C) for at least one hour (e.g., 1-200 hours) at a pressure of 101-2,500 kPa. In a more particular embodiment, the catalyst can be made to under steaming with 75-100% steam at 315°-500° C. and atmospheric pressure for 2-25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

In order to more fully illustrate the process of this invention and the manner of practicing same, the following examples are presented. Whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample g/100 g of calcined adsorbant. MCM-22 always exhibits Equilibrium Adsorption values of greater than about 10 wt.% for water vapor, greater than about 4.5 wt.%, usually greater than about 7 wt.% for cyclohexane vapor, and greater than about 10 wt.% for n-hexane vapor. These vapor sorption capacities are a notable distinguishing feature of zeolite MCM-22 and are preferred for the zeolite component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078; in the *Journal of Catalysis*. vol. 4, p. 527 (1965); vol. 6, p. 278 (1966); and vol. 61, p. 395 (1980), each incorporated herein by reference as to that description. The experimental conditions of the test used herein include a constant temperature of 538° C. and a variable flow rate as described in detail in the *Journal of Catalysis*, vol. 61, p. 395.

EXAMPLE 1

One part sodium aluminate (43.5% $Al_2O_3$, 32.2% $Na_2O$, 25.6% $H_2O$) was dissolved in a solution containing 1 part of 50% NaOH solution and lo3.13 parts $H_2O$. To this was added 4.50 parts hexamethyleneimine. The resulting solution was added to 8.55 parts of Ultrasil, a precipitated, spray-dried silica (90% $SiO_2$).

The reaction mixture had the following composition, in mole ratios:

| | | |
|---|---|---|
| $SiO_2/Al_2O_3$ | = | 30.0 |
| $OH^-/SiO_2$ | = | 0.18 |
| $H_2O/SiO_2$ | = | 44.9 |

|  |  |  |
| --- | --- | --- |
| Na/SiO$_2$ | = | 0.18 |
| R/SiO$_2$ | = | 0.35 | where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

|  |  |
| --- | --- |
| H$_2$O | 15.2 wt. % |
| Cyclohexane | 14.6 wt. % |
| n-Hexane | 16.7 wt. % |

The surface area of the zeolite was measured to be 494 m$^2$/g.

The chemical composition of the uncalcined material was determined to be as follows:

| Component | wt. % |
| --- | --- |
| SiO$_2$ | 66.9 |
| Al$_2$O$_3$ | 5.40 |
| Na | 0.03 |
| N | 2.27 |
| Ash | 76.3 |
| SiO$_2$/Al$_2$O$_3$, mole ratio | 21.10 |

TABLE E

| Degrees 2-Theta | Interplanar d-Spacing (A) | I/I° |
| --- | --- | --- |
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| Example | 3 | 4 | 5 |
| --- | --- | --- | --- |
| Synthesis Mixture, mole ratios |  |  |  |
| SiO$_2$/Al$_2$O$_3$ | 30.0 | 30.0 | 30.0 |
| OH$^-$/SiO$_2$ | 0.18 | 0.18 | 0.18 |
| H$_2$O/SiO$_2$ | 19.4 | 19.4 | 44.9 |
| Na/SiO$_2$ | 0.18 | 0.18 | 0.18 |
| R/SiO$_2$ | 0.35 | 0.35 | 0.35 |
| Product Composition, Wt. % |  |  |  |
| SiO$_2$ | 64.3 | 68.5 | 74.5 |
| Al$_2$O$_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| SiO$_2$/Al$_2$O$_3$, mole ratio | 22.5 | 20.9 | 26.0 |
| Adsorption, Wt. % |  |  |  |
| H$_2$O | 14.9 | 13.6 | 14.6 |
| Cyclohexane | 12.5 | 12.2 | 13.6 |
| n-Hexane | 14.6 | 16.2 | 19.0 |
| Surface Area, m$^2$/g | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a larger preparation of the required synthetic porous crystalline material 4.49 parts of hexamethyleneimine was added to a solution containing 1 00 parts of sodium aluminate, 1.0 part of 50% NaOH solution and 44.20 parts of H$_2$O. To the combined solution was added 8.54 parts of precipitated silica (Ultrasil VN3). The mixture was crystallized with agitation at 145° C. in a reactor and the product was water washed and dried at 120° C.

Product chemical composition (uncalcined) surface area and adsorption analyses results were as set forth in Table G:

TABLE G

| Product Composition |  |
| --- | --- |
| C | 12.1 wt. % |
| N | 1.98 wt. % |
| Na | 640 ppm |
| Al$_2$O$_3$ | 5.0 wt. % |
| SiO$_2$ | 74.9 wt. % |
| SiO$_2$/Al$_2$O$_3$, mole ratio | 25.4 |
| Adsorption, wt. % |  |
| Cyclohexane | 9.1 |
| N-Hexane | 14.9 |
| H$_2$O | 16.8 |
| Surface Area, m$^2$/g | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3g samples of the calcined material ion-exchanged 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions | Ionic Composition, wt. % | | |
|---|---|---|---|
| | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present synthetic porous crystalline material where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| $SiO_2/B_2O_3$ | = | 6.1 |
|---|---|---|
| $OH^-/SiO_2$ | = | 0.06 |
| $H_2O/SiO_2$ | = | 19.0 |
| $K/SiO_2$ | = | 0.06 |
| $R/SiO_2$ | = | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 240° C. and found to have the following sorption capacities:

| $H_2O$ (12 Torr) | 11.7 wt. % |
|---|---|
| Cyclohexane (40 Torr) | 7.5 wt. % |
| n-Hexane (40 Torr) | 11.4 wt. % |

The surface area of the calcined crystalline material was measured (BET) to be 405 $m^2/g$.

The chemical composition of the uncalcined material was determined to be as follows:

| N | 1.94 wt. % |
|---|---|
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio | 1406 |
| $SiO_2/(Al + B)_2O_3$, molar ratio | 25.8 |

EXAMPLE 12

A portion of the calcined crystalline product of Example 11 was treated with $NH_4Cl$ and again calcined. The final crystalline product was tested in the Alpha test and found to have an Alpha Value of 1.

EXAMPLE 13

This example illustrates another preparation of the synthetic porous crystalline material in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| $SiO_2/B_2O_3$ | = | 12.3 |
|---|---|---|
| $OH^-/SiO_2$ | = | 0.056 |
| $H_2O/SiO_2$ | = | 18.6 |
| $K/SiO_2$ | = | 0.056 |
| $R/SiO_2$ | = | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) 20 were measured:

| $H_2O$ | 14.4 wt. % |
|---|---|
| Cyclohexane | 4.6 wt. % |
| n-Hexane | 14.0 wt. % |

The surface area of the calcined crystalline material was measured to be 438 $m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al + B)_2O_3$, molar ratio | 28.2 |

EXAMPLE 14

A portion of the calcined crystalline product of Example 13 was tested in the Alpha Test and found to have an Alpha Value of 5.

EXAMPLE 15

A sample of MCM-22, which was prepared in accordance with the method of Example 7, above, was incorporated with alumina (65 wt. % MCM-22/35 wt. % alumina) to provide the catalyst for the following example. This mixture was extruded, crushed, and sized to 14/25 mesh.

EXAMPLE 16

The catalyst of Example 15 was charged to a reactor. Phenol was introduced to the reactor, which had been preheated to a temperature sufficient to keep the phenol liquefied. After the catalyst bed as flooded with phenol, propylene was introduced into the reactor. The temperature was raised to 130° C. at reaction conditions of 3:1 molar ratio of phenol to propylene, 7 hr$^{-1}$ WHSV, and 350 psig. After 34 hours on stream the reaction products were collected and analyzed. Table H below summarizes the results of the product analysis.

EXAMPLE 17

ZSM-12 was incorporated with alumina (65 wt. % ZSM-12/35 wt. % alumina) to provide the catalyst for this example. The mixture was extruded, crushed, and sized to 14/25 mesh.

This catalyst was charged to a reactor. Phenol was introduced to the reactor, which had been preheated to a temperature sufficient to keep the phenol liquefied. After the catalyst bed was flooded with phenol, propylene was introduced into the reactor. The temperature was raised to 150° C. at reaction conditions of 3:1 molar ratio of phenol to propylene, 7 hr$^{-1}$ WHSV, and 350 psig. After 5 hours on stream the reaction products were collected and analyzed. Table H below summarizes the results of the product analysis.

TABLE H

Comparison of MCM-22 and ZSM-12
65% Zeolite/35% Al$_2$O$_3$
3:1 Phenol:Propylene, 7 WHSV, 350 psig

| Zeolite | Temp. °C. | Propylene Conversion | Phenol Conversion | Isopropyl Phenol Selectivity* |
|---|---|---|---|---|
| MCM-22 | 130 | 64.0 | 22.9 | 77.8 |
| ZSM-12 | 150 | 60.7 | 18.7 | 40.2 |

*Molar Selectivity Based on Propylene Conversion

Phenol conversion and isopropyl phenol selectivity were calculated in accordance with the following formulae:

$$\text{Phenol Conversion} = \frac{(\text{wt \% phenol in feed}) - (\text{wt \% phenol in product})}{(\text{wt \% phenol in feed})} \times 100$$

$$\text{Isopropyl Phenol Selectivity} = \frac{\text{Moles of isopropyl phenol produced}}{\text{Moles of phenol converted}} \times 100$$

What is claimed is:

1. A process for the production of a relatively short chain alkyl-substituted phenolic compound which comprises contacting at least one alkylatable phenolic compound with at least one alkylating agent selected from the group consisting of olefins, alcohols, and alkyl halides, and possessing an alkylating aliphatic group having from one to five carbon atoms under alkylation reaction conditions and in the presence of an alkylation catalyst composition to provide an alkylated phenol possessing at least one alkyl group derived from said alkylating agent, said alkylation reaction conditions including a temperature between about 50° C. and about 500° C., a pressure between about 0.1 and about 100 atmospheres, a feed weight hourly space velocity of between about 0.1 and about 200 hr$^{-1}$, and an alkylatable phenolic compound to alkylating agent mole ratio of from about 0.1:1 to about 50:1; and said catalyst composition comprising a synthetic porous crystalline material characterized by an X-ray diffraction pattern including values substantially as follows:

| Interplaner d-Spacing (A) | Relative Intensity, I/I° × 100 |
|---|---|
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | M–M |
| 4.06 ± 0.07 | W–S |
| 3.91 ± 0.07 | M–VS |
| 3.42 ± 0.06 | VS |

2. The process of claim 1 wherein said synthetic porous crystalline material is characterized by an X-ray diffraction pattern including values substantially as follows:

| Interplanar d-Spacing (A) | Relative Intensity, I/I° × 100 |
|---|---|
| 30.0 ± 2.2 | W–M |
| 22.1 ± 1.3 | W |
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | W–M |
| 4.06 ± 0.07 | W–S |
| 3.91 ± 0.07 | M–VS |
| 3.42 ± 0.06 | VS |

3. The process of claim 1 wherein the synthetic porous crystalline material is characterized by an X-ray diffraction pattern including values substantially as follows:

| Interplanar d-Spacing (A) | Relative Intensity, I/I° × 100 |
|---|---|
| 12.36 ± 0.4 | M–VS |
| 11.03 ± 0.2 | M–S |
| 8.83 ± 0.14 | M–VS |
| 6.86 ± 0.14 | W–M |
| 6.18 ± 0.12 | M–VS |
| 6.00 ± 0.10 | W–M |
| 5.54 ± 0.10 | W–M |
| 4.92 ± 0.09 | W |
| 4.64 ± 0.08 | W |
| 4.41 ± 0.08 | W–M |
| 4.25 ± 0.08 | W |
| 4.10 ± 0.07 | W–S |
| 4.06 ± 0.07 | W–S |
| 3.91 ± 0.07 | M–VS |
| 3.75 ± 0.06 | W–M |
| 3.56 ± 0.06 | W–M |
| 3.42 ± 0.06 | VS |
| 3.30 ± 0.05 | W–M |
| 3.20 ± 0.05 | W–M |
| 3.14 ± 0.05 | W–M |
| 3.07 ± 0.05 | W |

-continued

| Interplanar d-Spacing (A) | Relative Intensity, I/I° × 100 |
|---|---|
| 2.99 ± 0.05 | W |
| 2.82 ± 0.05 | W |
| 2.78 ± 0.05 | W |
| 2.68 ± 0.05 | W |
| 2.59 ± 0.05 | W |

4. The process of claim 1 wherein the synthetic porous crystalline material zeolite is characterized by an X-ray diffraction pattern including values substantially as follows:

| Interplanar d-Spacing (A) | Relative Intensity, I/I° × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

5. The process of claim 1 wherein the synthetic porous crystalline material has a composition comprising the molar relationship:

$$X_2O_3:(n)YO_2$$

wherein X is a trivalent element selected from the group consisting of aluminum, boron, iron and gallium, Y is a tetravalent element selected from the group consisting of silicon and germanium, and n is at least 10.

6. The process of claim 2 wherein the synthetic porous crystalline material has a composition comprising the molar relationship:

$$X_2O_3:(n)YO_2$$

wherein X is a trivalent element selected from the group consisting of aluminum, boron, iron and gallium, Y is a tetravalent element selected the group consisting of silicon and germanium, and n is at least about 10.

7. The process of claim 3 wherein the synthetic porous crystalline material has a composition comprising the molar relationship:

$$X_2O_3:(n)YO_2$$

wherein X is a trivalent element selected from the group consisting of aluminum, boron, iron and gallium, Y is a tetravalent element selected from the group consisting of silicon and germanium, and n is at least about 10.

8. The process of claim 4 wherein the synthetic porous crystalline material has a composition comprising the molar relationship:

$$X_2O_3:(n)YO_2$$

wherein X is a trivalent element selected from the group consisting of aluminum, boron, iron and gallium, Y is a tetravalent element selected from the group consisting of silicon and germanium, and n is at least about 10.

9. The process of claim 1, wherein the synthetic porous crystalline material possesses equilibrium absorption capacities greater than about 4.5 weight percent for cyclohexane vapor and greater than about 10 weight percent for n-hexane vapor.

10. The process of claim 1 wherein said synthetic porous crystalline material has been treated to replace original cations, at least in part, with a cation or mixture of cations selected from the group consisting of hydrogen, rare earth metals, and metals of Groups IIA, IIIA, IVA, IB, IIB, IIIB, IVB, VIB and VIII of the Periodic Table.

11. The process of claim 10 wherein said synthetic porous crystalline material has been thermally treated in the presence or absence of steam at a temperature of up to about 925° C.

12. The process of claim 1 wherein said synthetic porous crystalline material has been thermally treated in the presence or absence of steam at a temperature of up to about 925° C.

13. The process of claim 1 wherein said catalyst composition includes a matrix material.

14. The process of claim 13 wherein said matrix material is selected from the group consisting of silica-containing material, alumina-containing material, zirconia-containing material, titania-containing material, magnesia-containing material, beryllia-containing material, thoria-containing material, and combinations thereof.

15. The process of claim 1 wherein said alkylatable phenolic compound is selected from the group consisting of phenol, methylphenols, dimethylphenols, ethylphenols, propylphenols, butylphenols, halophenols, dihydroxybenzenes, and hydroxylated fused ring compounds.

16. The process of claim 1 wherein said alkylating agent is selected from the groups consisting of ethylene, propylene, butenes, pentenes, methanol, ethanol, n-propanol, iso-propanol, butanols, pentanols, and alkyl halides.

17. The process of claim 1 wherein said alkylation reaction conditions include a temperature between about 100° C. to about 400° C., a pressure of from about 1 to 5 atmospheres, a feed WHSV of from about 1 to 50 hr$^{-1}$, and a mole ratio of alkylatable phenolic compound to alkylating agent of from about 0.5:1 to about 5:1.

18. The process of claim 1 wherein said alkylatable phenolic compound is phenol, the alkylation agent is propylene, and the alkylated phenol product is isopropyl phenol.

* * * * *